US012345749B2

(12) United States Patent
Annus et al.

(10) Patent No.: US 12,345,749 B2
(45) Date of Patent: Jul. 1, 2025

(54) DEVICE AND METHOD FOR MEASURING OF THE COMPLEX TRANSFER FUNCTION OF AN OBJECT

(71) Applicant: Tallinn University of Technology, Tallinn (EE)

(72) Inventors: Paul Annus, Tallinn (EE); Raul Land, Tallinn (EE); Mart Min, Tallinn (EE); Olev Märtens, Tallinn (EE); Marek Rist, Tallinn (EE); Eiko Priidel, Tallinn (EE)

(73) Assignee: Tallinn University of Technology, Tallinn (EE)

( * ) Notice: Subject to any disclaimer, the term of this patent is extended or adjusted under 35 U.S.C. 154(b) by 519 days.

(21) Appl. No.: 17/128,074

(22) Filed: Dec. 19, 2020

(65) Prior Publication Data

US 2021/0190841 A1 Jun. 24, 2021

(30) Foreign Application Priority Data

Dec. 19, 2019 (EE) ................................. P201900031

(51) Int. Cl.

*G01R 25/00* (2006.01)
*A61B 5/0537* (2021.01)
*G01R 25/04* (2006.01)

(52) U.S. Cl.

CPC .......... *G01R 25/005* (2013.01); *A61B 5/0537* (2013.01); *G01R 25/04* (2013.01)

(58) Field of Classification Search

CPC ... A61B 5/0537; A61B 5/7225; A61B 5/0809; A61B 5/053; A61B 5/024; G01R 25/005; G01R 25/04; G01R 27/16; G01R 27/28

USPC ........................... 702/109; 324/605; 600/547

See application file for complete search history.

(56) References Cited

U.S. PATENT DOCUMENTS 4,940,060 A * 7/1990 Gu ......................... A61H 39/02 600/548
7,970,461 B2 6/2011 Kink et al.
10,063,369 B1 * 8/2018 Murphy ............... A61B 5/7225
11,158,944 B2 * 10/2021 Schrattenecker ..... G01S 13/343

(Continued)

FOREIGN PATENT DOCUMENTS

EP 0256887 A2 * 2/1988 ............... A61B 5/00
EP 1701459 A1 * 9/2006 .......... H03M 1/1205

OTHER PUBLICATIONS

Paavle, T. et al., "Aspects of Using Chirp Excitation for Estimation of Bioimpedance Spectrum", In: Fourier Transform—Signal Processing, Ed. Salih Salih, InTech, Apr. 2012, pp. 237-256.

(Continued)

*Primary Examiner* — Alex M Valvis
*Assistant Examiner* — Jonathan E. Cooper
(74) *Attorney, Agent, or Firm* — Meunier Carlin & Curfman LLC

(57) ABSTRACT

The invention is related to the field of measurement electronics and related to the measurement of complex transfer functions (e.g. of impedance), especially in the presence of large disturbances and for measuring of small changes of the characteristics of the object under test. The goals of the proposed invention are achieved by detuning of the excitation and reference signals, e.g. by adding incremental phase-shift to the excitation signal to generate the reference signal.

9 Claims, 3 Drawing Sheets

(56) References Cited

U.S. PATENT DOCUMENTS

| | | | | |
|---|---|---|---|---|
| 11,517,216 | B2 * | 12/2022 | Cho | G01N 27/028 |
| 2005/0283091 | A1 * | 12/2005 | Kink | A61B 5/0537<br>600/547 |
| 2009/0221900 | A1 * | 9/2009 | Ikushima | A61B 5/7203<br>600/409 |
| 2010/0237851 | A1 * | 9/2010 | Coster | G01R 27/28<br>324/76.19 |
| 2011/0301492 | A1 * | 12/2011 | Lamp | A61B 5/0535<br>600/547 |
| 2018/0055437 | A1 * | 3/2018 | Nakayama | A61B 5/74 |
| 2018/0067063 | A1 * | 3/2018 | Cherkassky | G01R 19/0038 |
| 2018/0325414 | A1 * | 11/2018 | Marashdeh | A61B 5/0033 |

OTHER PUBLICATIONS

Annus, P. et al., "Design of a Bioimpedance Measurement System Using Direct Carrier Compensation", Published in: Proceedings of the 2005 European Conference on Circuit Theory and Design, IEEE, 2005, vol. 3, pp. 23-26, DOI: 10.1109/ECCTD.2005.1523051.

* cited by examiner

DEVICE AND METHOD FOR MEASURING OF THE COMPLEX TRANSFER FUNCTION OF AN OBJECT

PRIORITY

This application claims priority of Estonian patent application number P201900031 filed on Dec. 19, 2019 the contents of which is fully incorporated herein by reference.

TECHNICAL FIELD

The invention belongs to the field of electronics and is related to the measurement of the response signal caused by the excitation signal applied to the object under study and to the further processing of the obtained results for measuring the complex transfer function. The main application field of the proposed invention is to be used in measuring and other devices, where the measurements or the operation of the device depends on the presence of large disturbances or where the determination of small changes in the measured value of a high base value is performed. Typically, such a device is an impedance (resistance) or conductivity meter in which a known current is passed through the object, material or tissue being measured, or a current that is constantly monitored and the voltage drop across the object is measured.

BACKGROUND

Complex impedance measurement is used, for example, to monitor heart rate and respiration, with interest in measuring and monitoring very small variations of the signals due to cardiac or respiratory activity (of the order of 100 to 1000 or more times smaller, compared to the baseline value of complex impedance or conductivity specific to organs and tissues). Furthermore, the measurement is often complicated due to noise and disturbances A solution of synchronous measurement using cross-correlation (Wiener-Khinchin theorem) is known and common in the art (U.S. Pat. No. 7,970,461, T. Paavle et al "*Aspects of Using Chirp Excitation for Estimation of Bio-impedance Spectrum*," in Fourier Transform—Signal Processing, S. Salih, Ed. InTech, 2012). To achieve this at a single frequency, the response signal can be multiplied by the normalized sinusoidal excitation signal and the normalized excitation signal by the quadrature signal (synchronous demodulation) and the results obtained are further filtered. For multi-frequency measurements, the described steps should be repeated for each frequency separately. It is also possible to use waveforms other than sinewaves and their sums. Further, the obtained result can be used in the operation of the device to determine, for example, the module of and the phase the response signal with respect to the excitation signal.

Also a solution is known (P. Annus et al, "Design of a bioimpedance measurement system using direct carrier compensation," in *Proc. of the European Confer. on Circuit Theory and Design*: Cork, Ireland, 28 Aug.-2 Sep. 2005: Piscataway, NJ, 2005, vol. 3, pp. 23-26), which contains compensation of the response signal received from the system under study by adding a signal of the same magnitude to it—with the opposite phase. Ideally, the base value of the response signal is after compensation zero (or close to zero in real applications), not interfering with the detection of small changes. The problem is to determine the magnitude and phase of the compensating signal, on what the accuracy of the compensation depends.

Usually, in order to find the complex value of the impedance of the object under study (presented either as the real and the imaginary parts, or as a modular-phase pair), either two parallel measurement channels are used, or the single channel is switched to measure one and then the other part of the complex quantity.

The closest solution known in the prior art is U.S. Pat. No. 7,970,461, wherein a periodic excitation signal is applied to the object under test and the response signal received from the object under study is multiplied by a reference signal, delayed by a fixed phase shift. The value of this phase shift is selected according to the expected characteristics of the object at a frequency of interest.

This solution is not suitable for measurement if the expected approximate characteristics of the object under study (i.e. if the approximate amount of the suitable delay) is not known in advance.

So there is a need for a method that is suitable to be used with an object which (even not approximate) properties are not known.

SUMMARY OF THE INVENTION

The objectives of the invention are achieved by a device as claimed in the appended claims. Accordingly, it is an object of this invention to provide a device for measuring the complex transfer function of an object, comprising a generator for generating an AC excitation signal and an AC reference signal, a multiplier for multiplying a response (from the object) signal and a reference signal, a low pass filter connected to the output of the multiplier and a data processing unit connected to its output, wherein the generator is configured to generate the excitation signal and the reference signal in such way, that the reference signal is tuned away (detuned) from the excitation signal so that the delay of the reference signal relatively to the excitation signal increases (in discrete steps or continuously) so that at a beginning and at an end of a measurement period the excitation signal and the reference signal coincide.

The invention according to one example embodiment is disclosed, wherein the delay of the reference signal with respect to the excitation signal is implemented by an increasing phase shift.

The invention according to the second embodiment example is disclosed, according to which the delay of the reference signal with respect to the excitation signal is performed by means of the difference between the frequencies of the reference signal and the excitation signal.

The corresponding methods according to the invention are disclosed herein as well. Thus, it is an object of this invention to provide a method for measuring the complex transfer function of an object, comprising the steps of: generating an alternating voltage excitation signal which is fed to the object to be measured; generating an AC reference signal; a response signal generated by the excitation signal is received from the object to be measured; the response signal is multiplied by the reference signal, which differs in that the reference signal is tuned with respect to the excitation signal so that during the measurement cycle the reference signal is increasingly delayed (in discrete steps or continuously) relatively to the excitation signal so, that at a beginning and at an end of a measurement cycle the excitation signal and the reference signal coincide.

Compared to the closest known solution, where the impedance characteristic values are measured at two preselected fixed time offsets, the measurement according to the proposed invention takes many phase offsets in the range from 0 to 2π, wherein the module and phase of the complex transfer function are determined from the multiplication curve of the response signal and reference signal. So the most appropriate sampling time instances to measure the small result variations are selected by practical and metrological suggestions.

BRIEF DESCRIPTION OF THE DRAWINGS

Implementation examples of the invention are described below with references to the accompanying drawings, in which.

DETAILED DESCRIPTION THE INVENTION

Figure 1:
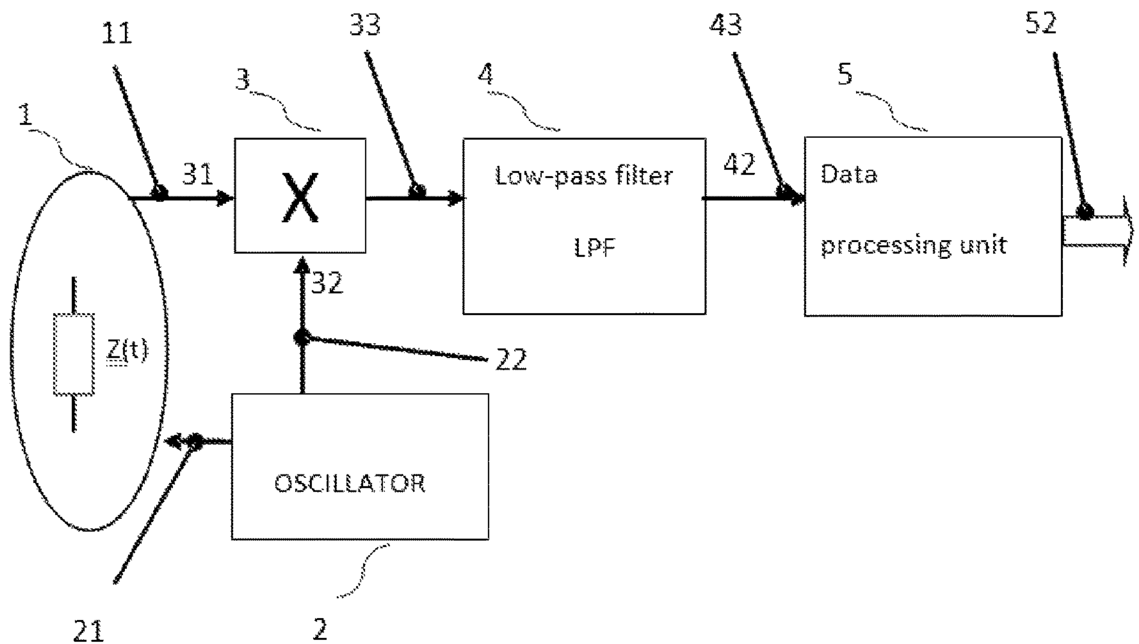
FIG. 1 is a block diagram of a device according to an embodiment of the invention.

One embodiment of the invention is shown in the FIG. 1. A device for measuring the complex transfer function of an object 1, e.g. a bio-object, e.g. electrical impedance or conductivity, comprises a generator 2 configured to generate an AC excitation signal 21 and a reference signal 22, a multiplier 3, a low pass filter 4 and a data processing unit 5.

The device works as follows. The alternating voltage excitation signal 21 generated by the generator 21 is applied to the object to be measured 1 and the object response signal 11 is applied to the input 31 of the multiplier 3. The reference signal 22 generated by the generator is applied to the second input 32 of the multiplier. The output signal 33 of the multiplier 3 is fed to a low pass filter 4, which suppresses the high frequency and noise components of the output signal 33 and separates the low frequency components, characterizing the properties of object 1.

On the basis of the excitation signal 21 in the generator 2 a reference signal 22 is formed, which is tuned away ("detuned") from the excitation signal 21 so, that during the measurement cycle the reference signal delay increases (relatively to the excitation signal 21) in discrete steps or continuously so, that the excitation signal 21 and the reference signal 22 coincide at the beginning and the end of the measurement cycle. According to one embodiment, the sinusoidal reference signal is generated as follows: after each predetermined integer excitation signal sampling period nT (n=1, 2, 3, 4, . . . ), a certain phase shift Δϕ is added to the phase of the reference signal. The value of the phase shift Δϕ is determined by the relationship (1):

$$\Delta\phi=360/p*i, \quad (1)$$

where p is the repeat-rate, (i.e. the number of steps during which Δϕ becomes equal to 2π) and i=0 . . . p−1.

Such periodically varying phase offset of the excitation signal and the reference signal provides a variable frequency (f=1/Tp) signal at the output 42 of the lowpass filter 4, the amplitude of which depends on the excitation signal frequency and phase shift Δϕ values, as well as on the complex transfer function and static and dynamic values of it (reflecting impedance, conductivity).

After multiplying and filtering the reference signal and the response signal, a periodic signal (preferably 300 Hz to 3 kHz) is formed at the output 42 at a repeat-rate defined by the excitation rate of the excitation signal 21 and the reference signal 22, from which static and dynamic parameters 52 are determined in the data processing unit 5 from the complex transfer function.

In a preferred embodiment of the data processing unit, the input signal 43 is sampled at such phase shift values Δϕ, at which the baseline measurement value of the alternating component at f=1/Tp is minimal, so allowing additional gain to be applied in the proposed solution without suppression or compensation of the baseline value. So improved determination of the impedance (conductivity) static and dynamic parameters, even if they are significantly (hundreds, thousands or more times) lower than the baseline value of the signal, is achieved.

The advantage of the invention is that the measurement of a complex transmission, i.e. its real and imaginary part (e.g. active and reactive resistance) takes place in a single measurement channel due to the continuous phase separation of the excitation signal and the reference signal.

In a preferred embodiment, a reference signal 22 is generated, differing from the excitation signal 21 (typically 10 kHz to 10 MHz for a bio-object; it is clear to one skilled in the art that the reference signal frequency is selected according to the object and may be much higher or lower). For example, in accordance with established practice, it has been considered technically reasonable to select a phase separation frequency range of 300 Hz to 3 kHz for impedance measurements affected by cardiac activity, to monitor higher harmonics up to about 50 harmonics. It will be clear to a person skilled in the art that, depending on the nature of the object under study and the phenomenon under study, a much lower or higher repeat-rate may be chosen.

In another preferred embodiment, a reference signal 22 is generated with a different than the excitation signal frequency 21. In the case of a bio-object, f=ω/2π is usually selected from 10 kHz to 10 MHz. It is clear to the person skilled in the art that the reference signal frequency can be significantly higher or lower than in the case of bio-objects. A certain frequency shift (usually Δf=Δω/2π=300 Hz to 3 kHz for cardiac monitoring) is selected, to give required repeat-rate. The corresponding relation is described by equation 2.

$$r(t)=\sin((\omega+\Delta\omega)*t) \quad (2)$$

where r (t) is the excitation signal,

ω is the frequency of the excitation signal,

Δω is the frequency offset (detuning value) and t is the current time

Figure 2:
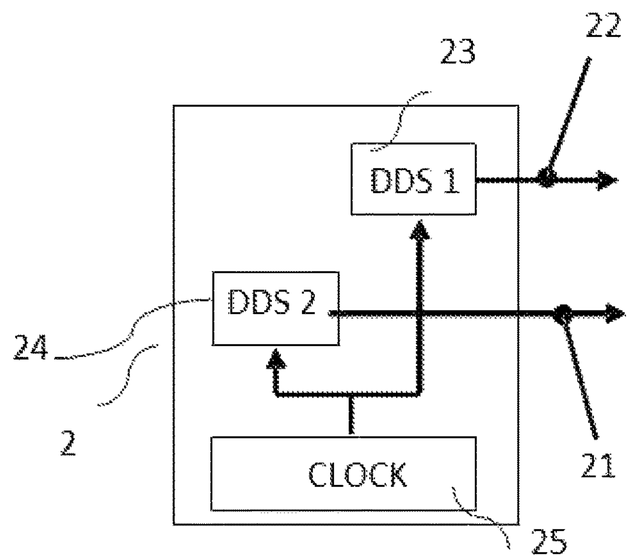
FIG. 2 is a block diagram of a generator used in the invention.

One embodiment of the generator 2 is shown in the FIG. 2. The generator 2 comprises two DDSs (direct digital synthesizers) 23 and 24 controlled by pulses of a reference clock 25. One DDS is configured to generate an excitation signal 21 and the other DDS being configured to generate a reference signal 22, according to the above embodiment examples.

According to another embodiment, the generator 2 may be implemented as a tabulated function of a pre-recorded periodic waveform (e.g.: sine signal, binary signal), from which the instantaneous values of the signal are read out at variable delay rates.

Figure 3A:
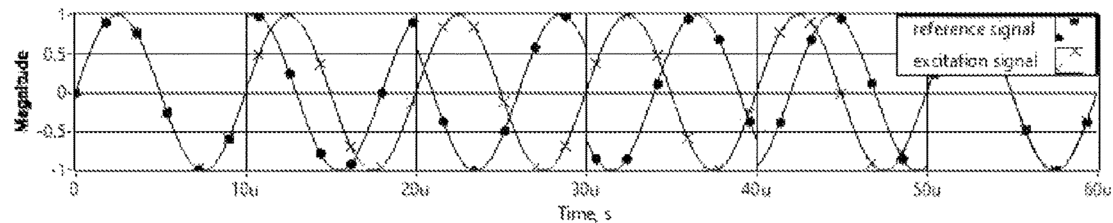
FIGS. 3A, 3B and 3C show the waveforms (and their arrangement in relation to each other) of the excitation, reference and response signals and the same for the multiplication product of response and reference signals used in the device and method according to the invention.
Figure 3B:
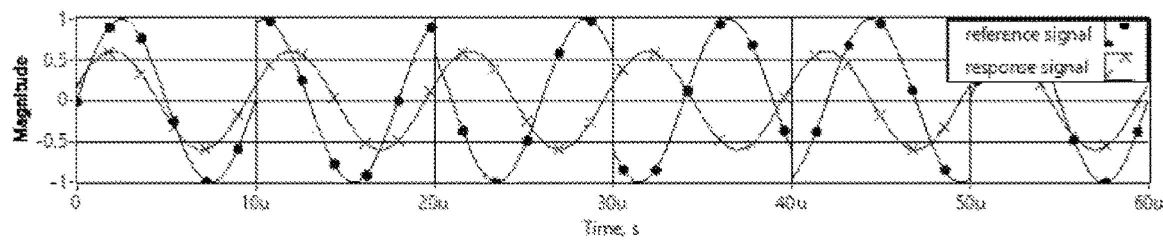
Figure 3C:
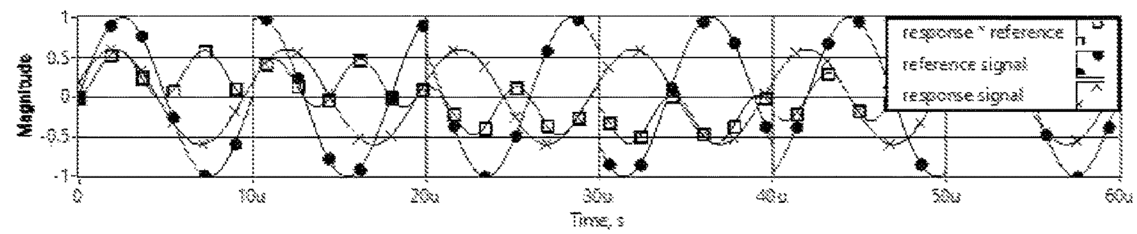

FIGS. 3 and 4 illustrate the waveforms and arrangement (in relation to each other) of the excitation, reference and response signals and the response and reference signals used in the device and method, according to the two embodiments described above. In the example of FIG. 3, the excitation signal frequency is 100 kHz and the repeat-rate is 6 (preferably p=300 to 3000 in real bioimpedance measurement applications). In the FIG. 3A the waveforms and arrangement (relatively to each other) of the reference signal and the excitation signal are shown. In the FIG. 3B the waveforms and arrangement of the reference signal and the response signal, their waveforms and arrangement relatively to each other are shown. In the FIG. 3C the waveforms and arrangements of the response signal, the reference signal and the product of the response and reference signal relatively to each other are given. As shown in this Figure, the reference signal and the excitation signal are triggered simultaneously, but the reference signal is applied to the excitation signal with increasing phase shift with respect to the excitation signal with each subsequent time interval. It can also be seen that the response signal is delayed with respect to the excitation signal due to the complex transmission (impedance or conductivity) contained in the reactive component of the object. The product of the response and the reference signal oscillates at twice of the frequency with respect to the excitation and reference signals, the amplitude of which in turn oscillates with a five-fold period with respect to the excitation signal. The product of the reference signal and the response signal is fed to a low-pass filter, which suppresses the high-frequency components of the signal. The maxima of the low-frequency signal here indicate the moment when the response signal and the reference signal are in the same phase, i.e. their product is proportional to the real part of the complex transmission of the object (for example, the active resistance). At the zero point of the low frequency signal, the response signal and the reference signal have a phase shift of 90 degrees, i.e. at this point the response signal is proportional to the imaginary part of the complex transmission (e.g. reactive resistance).

In the example of FIG. 4, the excitation signal frequency is 100 kHz (in real bioimpedance measurement applications between 10 kHz and 10 MHz) and the reference signal frequency is 16.7 kHz (thus 16.7 kHz resolution; in real bioimpedance measurement applications 300 Hz to 3 kHz). The waveforms and their arrangement (and their arrangement in relation to each other) of the excitation, reference and response signals and the response and reference signal product used in the devices and method according to the second embodiment are given there.

Figure 4A:
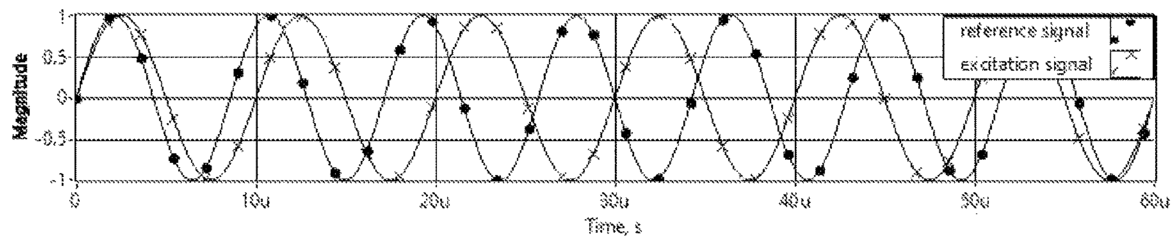
FIGS. 4A, 4B and 4C show the waveforms (and their arrangement in relation to each other) of the excitation, reference and response signals and of the multiplication product of response and reference signals used in the device and method according to the second embodiment of the invention.
Figure 4B:
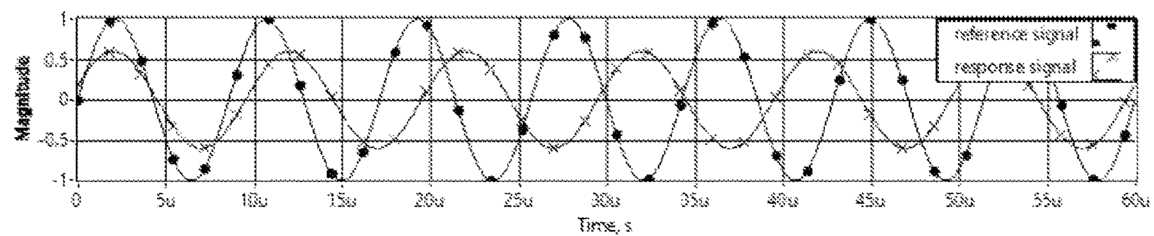
Figure 4C:
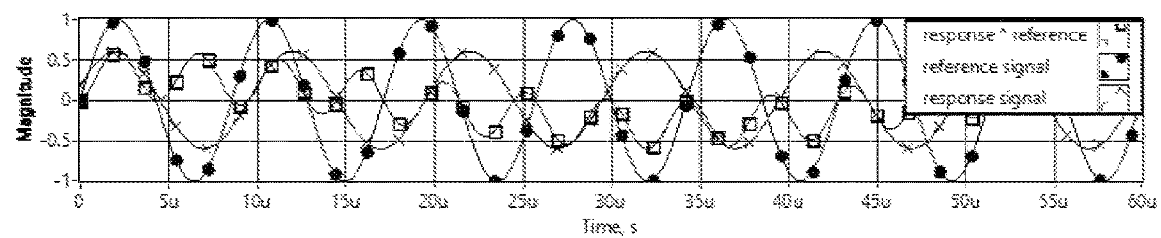

In the FIG. 4A the waveforms and arrangement (relatively to each other) of the reference signal and the excitation signal are shown. In the FIG. 4B the waveforms and arrangement of the reference signal and the response signal, their waveforms and arrangement relatively to each other are shown. In the FIG. 4C the waveforms and arrangements of the response signal, the reference signal and the product of the response and reference signal relatively to each other are given. As shown in the figure, the reference signal and the excitation signal are triggered simultaneously, but due to the difference in their frequencies, an incremental phase shift occurs between them, which increases to $2\pi$ over six periods (i.e., the phase shift returns to zero). The product of the response and the reference signal oscillates at twice the frequency with respect to the excitation and reference signals, the amplitude of which in turn oscillates with a five-fold periods with respect to the excitation signal. The product of the reference signal and the response signal is fed to a low-pass filter, which suppresses the high-frequency components of the signal. From the maxima and zeros of the low frequency signal, the complex transfer values are determined as described above.

In order to determine the complex transmission of the object, e.g. impedance or conductivity, both the response signal and the product of the response signal and the filtered reference signal are preferably stored in digital form. This enables to determine the time instances suitable for sampling from the product of the filtered reference signal and to calculate the real and imaginary parts of the complex transfer function from the appropriately acquired response and excitation signals, as well as to compensate the baseline value of the complex transfer function to determine the small changes in the complex transfer function.

In the embodiments described above, sinusoidal signals are used. Instead of sine signals, multisine signals can be used, but also square-wave signals, including so-called shortened square-wave signals, the generation of which is simpler and less energy consuming than the generation of sine signals. The solutions described above are suitable for use in portable devices, such as sports or health watches, in which heart rate and respiration parameters are detected by measuring bioimpedance, for example to monitor the shape of a heart wave and determine its parameters.

It is to be understood that the above description and appended drawings shall be interpreted as illustrative and not in a limiting sense. Those skilled in the art will appreciate that variations and modifications may be made to the illustrative examples without departing from the scope of the invention.

The invention claimed is:

1. A device for measuring a complex transfer function of an object, comprising:

a generator comprising a first and a second direct digital synthesizers (DDSs), the first direct digital synthesizer (DDS) configured to generate an AC excitation signal to be introduced into an object and the second direct digital synthesizer (DDS) to generate an AC reference signal;

a multiplier configured to multiply a response signal from the object and the AC reference signal from the generator; and a data processing unit connected to an output of the multiplier, wherein the generator is configured to generate the AC reference signal and the AC excitation signal during a measurement period, wherein the AC reference signal and the AC excitation signal coincide in phase at the beginning of said measurement period, and the AC reference signal has a discrete stepwise or a continuously increasing delay relative to the AC excitation signal during the measurement period until the AC excitation signal and the AC reference signal coincide again in phase at an end of the measurement period.

2. The device according to claim 1, wherein said AC reference signal and said AC excitation signal have equal frequencies and in order to delay the AC reference signal with respect to the AC excitation signal, the device being configured to add a phase shift to the phase $\Delta\Phi$ of the AC reference signal at least once at each predetermined period nT of the AC excitation signal, while n=1,2,3,4, . . . , where said phase $\Delta\Phi$=i* 360 /p, where p is the number of steps during which said phase $\Delta\Phi$ becomes equal to $2\pi$and i=0, 1, 2, . . . p−1.

3. The device according to claim 1, wherein a frequency of the AC reference signal is selected to be different from frequency of the AC excitation signal in order to delay the AC reference signal with respect to the AC excitation signal.

4. The device according to claim 3, wherein the frequency of the AC excitation signal is selected to be in a range of 10 kHz to 10 MHz, and the frequency of the AC reference signal differs from the frequency of the AC excitation signal by 300 Hz to 3 kHz.

5. The device according to claim 1, wherein the AC reference signal is tuned away from the AC excitation signal during the measurement period until the AC excitation signal and the AC reference signals coincide again in phase at an end of the measurement period.

6. A method for measuring the complex transfer function of an object with the device of claim 1, the method comprising the steps of:

generating an AC excitation signal by the first direct digital synthesizer (DDS) and feeding the signal to the object to be measured;

generating an AC reference signal by the second direct digital synthesizer (DDS);

receiving, by the multiplier, an AC response signal generated by the AC excitation signal from the object to be measured;

multiplying, by the multiplier, the AC response signal by the AC reference signal, wherein the AC reference signal is tuned with respect to the AC excitation signal so that during a measurement cycle the AC reference signal is increasingly delayed in discrete steps or continuously relative to the AC excitation signal so that at a beginning and at an end of the measurement cycle the AC excitation signal and the AC reference signal coincide.

7. The method according to claim 6, wherein to delay the AC reference signal relative to the AC excitation signal, a phase shift is added by the device to the phase $\Delta\Phi$ of the AC reference signal at least once for each predetermined period nT of the AC excitation signal, while n=1,2,3,4, . . . , where $\Delta\Phi$=i* 360/p and p is the number of steps during which $\Delta\Phi$ becomes equal to $2\pi$, while i=0. . . p−1.

8. The method according to claim 6, wherein a frequency of the AC reference signal is selected to be different from a frequency of the AC excitation signal in order to delay the AC reference signal with respect to the AC excitation signal.

9. The method of claim 8, wherein the frequency of the AC excitation signal is selected to be in a range of 10 kHz to 10 MHz, and the frequency of the AC reference signal is selected to be 300 Hz to 3 kHz different from the frequency of the AC excitation signal.

* * * * *